United States Patent
Blake et al.

[11] Patent Number: 5,874,110
[45] Date of Patent: Feb. 23, 1999

[54] ENTRAPPING ADDITIVES IN CARBOHYDRATE BODIES

[75] Inventors: Andrea S. Blake, Chantilly, Va.;
Robert K. Yang, Flushing, N.Y.;
Richard C. Fuisz, McLean, Va.

[73] Assignee: Fuisz Technologies Ltd., Chantilly, Va.

[21] Appl. No.: 898,306

[22] Filed: Jul. 22, 1997

[51] Int. Cl.[6] ........................................ A61K 9/14
[52] U.S. Cl. ................... 424/488; 424/499; 424/489; 424/490; 424/493; 514/951; 514/963
[58] Field of Search ..................... 424/489, 490, 424/493, 499, 488; 514/963, 951

[56] References Cited

U.S. PATENT DOCUMENTS

| | | | |
|---|---|---|---|
| 5,486,507 | 1/1996 | Whistler | 514/54 |
| 5,518,730 | 5/1996 | Fuisz | 424/426 |
| 5,549,917 | 8/1996 | Cherukuri et al. | 426/96 |
| 5,597,416 | 1/1997 | Fuisz et al. | 127/30 |
| 5,601,076 | 2/1997 | Battist et al. | 127/58 |

Primary Examiner—Thurman K. Page
Assistant Examiner—Lakshmi S. Channavajjala
Attorney, Agent, or Firm—Sandra M. Nolan

[57] ABSTRACT

The present invention is a method of entrapping an additive within carbohydrate bodies. The additive is drawn into the internal structure as a fluid during transformation of the bodies from a substantially amorphous state to a crystalline state. The present invention is also a delivery system including a carbohydrate body having an internal free volume space defined by an at least partially crystalline structure at equilibrium conditions, and an additive loaded within the carbohydrate body.

23 Claims, 2 Drawing Sheets

ENTRAPPING ADDITIVES IN CARBOHYDRATE BODIES

BACKGROUND OF THE INVENTION

Specialized processes for physically combining materials are often used in the food and pharmaceutical fields. The advantages of providing comestibles units which deliver more than one ingredient at a time are clear. Such advantages include lower cost, greater efficiency of production and ease of consumption (e.g., ingestion).

Various processes are conventionally used to make such units.

U.S. Pat. No. 5,486,507 to Whistler, incorporated herein by reference, covers porous spherical starch granules whose surfaces contain additives which can be released when rubbed.

U.S. Pat. No. 5,518,730 to Fuisz, also incorporated by reference, shows the melt-spinning of biodegradable polymers and bio-affecting agents to yield controlled release dosage systems.

These and other patents owned by the assignee of this invention deal with processes for treating ingredients for bio-affecting and other formulations in order to enhance the storage, delivery, or handling of the ingredients and/or the final products.

Commonly owned U.S. Pat. No. 5,549,917, incorporated herein by reference, discloses the making of a "solloid" by combining a solid non-fat substrate having an active associated therewith and a solid fat solidifiable at room temperature and subjecting the combination to disruptive forces sufficient to form and maintain a spheroidal solid.

U.S. Pat. No 5,597,416, also co-owned herewith, describes bi-dimensionally stabilized crystalline sugar structures which, while amorphous, are loaded with a non-solvent liquid. These structures are elongated and are made from feedstocks which incorporate crystallization modifiers, such as water or surfactants.

Another form of material processing is disclosed in copending commonly owned U.S. application Ser. No. 08/330,412, filed Oct. 28, 1994, entitled LIQUIFLASH PARTICLES AND METHOD OF MAKING SAME. This application discloses "liquiflash" processing, in which a feedstock is reduced to a condition wherein substantially all resistance to liquid flow is removed in an area localized to a processing barrier. A force is applied to the flowing feedstock in an amount sufficient to divide the material into discrete particles. This application, also, is incorporated herein by reference.

There remains a need for effective processes for combining materials, which processes yield combinations which are safe and useful in a variety of fields, but especially in the food and pharmaceutical fields.

SUMMARY OF THE INVENTION

The present invention is a process for combining materials by entrapping (or loading) non-solubilizing additives into pure, untreated spherical carbohydrate bodies (or particles), methods of making the resultant combined bodies and delivery systems containing same. The carbohydrate bodies must be capable of undergoing a transition from a substantially amorphous structure to a more crystalline one while in the presence of the additive.

Generally, a non-solubilizing additive, in fluid condition, is contacted with pure untreated carbohydrate bodies while they are "substantially amorphous". The fluid additive, preferably a hydrophobic liquid, is contacted with the unadulterated particles using a suitable technique, preferably immersion.

Originally, the carbohydrate bodies are substantially amorphous. They are made to undergo a transformation to a more crystalline state while in contact with the additive. The additive is entrapped or imbibed into spaces within the carbohydrate bodies. Generally, the additive promotes crystallization of the bodies. Flavor oils are preferred additives. Organoleptic and active ingredients are also preferred additives.

While the carbohydrate bodies are undergoing transformation from a substantially amorphous state to a more crystalline one, the additive penetrates into the bodies and becomes entrapped inside internal spaces in the bodies, which spaces are more evident as crystallization proceeds. The additive is bound into the internal polycrystallite structure of the bodies as a result of chemical and physical forces.

The invention eliminates the need for heat, solvents and other costly or complex features commonly used when combining substances conventionally.

BRIEF DESCRIPTION OF THE DRAWINGS

Various aspects of the invention are shown in the accompanying figures, which show images as follows.

DETAILED DESCRIPTION OF THE INVENTION

Figure 1A:
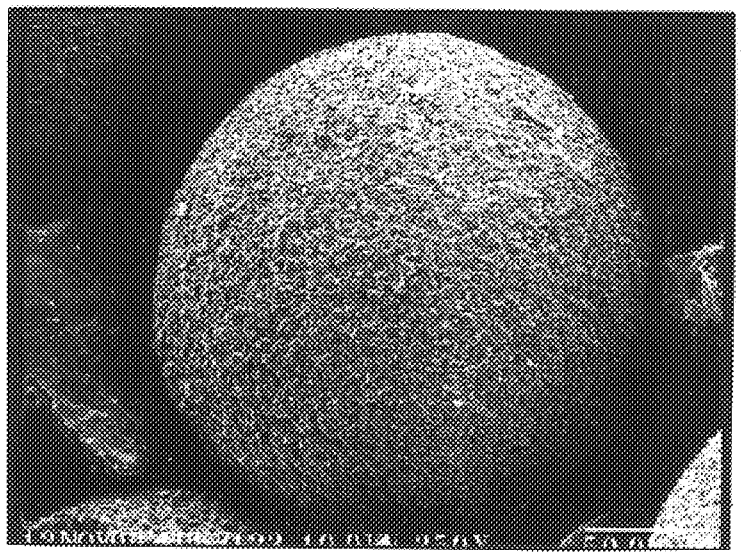
FIG. 1A is an electron micrograph, at 350× magnificatlion, of an intact crystalline sucrose microspheres.

The invention is a method for loading pure untreated spherical carbohydrate bodies capable of forming at least partially crystalline structure at equilibrium condition, i.e., at standard temperature, pressure and humidity.

The substantially pure untreated bodies are spherical and are composed of a carbohydrate which, when rendered amorphous, undergoes self-transformation from a substantially amorphous state to a more crystalline one. Sugars are suitable carbohydrates.

The bodies are "substantially pure" in that they do not contain additives. Such as crystallization modifiers or other agents which affect, in any way either the crystallization of the bodies or the entrapment of the liquid. Water, surfactant, and other known crystallization modifiers are excluded from the feedstock from which the carbohydrate bodies are made.

The bodies are "untreated" in that no non-carbohydrate ingredient is contacted with them before they are contacted with the fluid additive(s) to be entrapped therein.

The bodies to be treated are spherical in shape. Spheres and other spheroidal particles can be used. Shearlite microspheres, as described hereinbelow, are very useful.

The entrapment method includes contacting substantially amorphous spherical carbohydrate bodies with a fluid, i.e., a liquid or a gas, while the bodies undergo an internal transformation from an amorphous state to an equilibrium state which is characterized by a greater crystallinity than it had originally. While the carbohydrate bodies contact the fluid material during transformation, the fluid is imbibed into the bodies before the bodies reach an equilibrium state.

Ideally, the carbohydrate bodies will be kept under conditions of temperature, pressure and humidity that inhibit crystallization prior to contacting them with the fluid to be entrapped therein.

Another element of the present invention is an additive which is in the form of a fluid, i.e., a liquid or gas. The additive fluid must be capable of being imbibed, or absorbed, and retained in the interior crystalline structure of the transformed carbohydrate body. Further, the additive must not solubilize, or dissolve, the bodies. Although the presence of trace amounts of water appears to hasten crystallization of the amorphous bodies, anhydrous fluids are very effective in the entrapment process. Pure anhydrous oils are useful.

Useful additive fluids include flavor oils, long chain alcohols having at least a 4:1 ratio of carbon atoms to Hydroxyl groups, aliphatic and aromatic hydrophobic solvents, aliphatic and aromatic fatty acids, and combinations thereof.

Typically, flavor oils are imbibed in substantially amorphous spherical carbohydrate bodies, while they undergo transformation to a more crystalline state, by immersing the bodies in the oil. Flavor oils can be used alone or in combination with other oils, and, preferably, promote loading by initiating and driving the transformation of the carbohydrates from the amorphous to crystalline state. For instance, highly volatile flavor oils such as peppermint, spearmint, and orange can be used. Such oils are easily imbibed, and are believed to actually catalyze crystallization of amorphous sucrose.

Alternatively, the oil or other fluid is contacted with the surfaces of the spherical bodies (e.g., by spraying or other coating methods) and the treated bodies are stirred or otherwise mixed with the fluid. The mixture results in a coating of fluid onto the bodies' surfaces. The fluid in the coating is then imbibed or entrapped into the bodies.

While not wishing to be bound by a particular theory, Applicants believe that, during the carbohydrate bodies' transformation, the oil softens the interstices of the bodies and enhances penetration of the oil between micromolecular fissures in the transforming bodies. The resulting softened, or plasticized, matrix of carbohydrate molecules then realigns itself to form a new more crystalline structure. However, the crystalline habit formed in the presence of the oil or other fluid is different from that formed in its absence. The spaces created between crystallites in the structure provide a place for internal adsorption and entrapment of flavor oils or other additives. When treating microspheres, oil is absorbed into the spherical bodies while adsorbing onto and between crystallites within the polycrystallite microspheres' structures.

While not being bound by any particular theory, Applicants believe that the spaces formed as the carbohydrate bodies crystallize in the presence of the additive(s) exist both on an inter- and intra-molecular level. The creation of rearranged interior spaces results from the bodies' molecular matrices being transformed from a more randomly oriented array of molecules to a more highly ordered crystalline array. The rearrangement of spaces leads to the opening of "new" spaces, which serves to imbibe the fluid molecules which are in contact with the carbohydrate bodies. The fluid is drawn into the spaces and becomes entrapped and bound therein.

The phrase "substantially amorphous" refers to the state in which that the solid untransformed carbohydrate bodies do not exhibit any discernable crystalline structure when viewed with the light or electron microscope.

By "fluid", applicants mean that the additive is, or is associated with, a liquid or gaseous medium. It is preferred that the additive be a liquid or a mixture/solution of an additive in a liquid.

Preferred fluids are hydrophobic. Due to the aqueous solubility of many carbohydrates, water, steam and other hydrophilic fluids should be avoided. Ideally, the transformation process occurs in the absence of hydrophilic fluids.

One or more additional agents may also be incorporated in the additive liquid. Such agents can include bio-affecting ingredients and/or organoleptic ingredients. A non-limiting list of bio-affecting ingredients is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, ant-infectives, psycho-tropics, antimanics, stimulants, gastrointestinal agents, sedatives, antidiarrheal preparations, anti-anginal drugs, vasodilators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs, proteins, peptides, other biologically based additives, and mixtures thereof.

Ideally, the carbohydrate bodies are formed of a sugar. "Sugars" as used herein means one or more substances based on simple crystalline mono- and di-saccharide structures, i.e., based on $C_5$ and $C_6$ sugar configurations. Applicants contemplate the use of a variety of sugars, including sucrose, fructose, lactose, maltose, and sugar alcohols such as sorbitol, mannitol, maltitol, etc. and mixtures. Sucrose is preferred.

The primary requirement for the carbohydrate bodies is that they be capable of transforming to an at least partially crystalline structure at equilibrium conditions. Equilibrium conditions are generally considered standard temperature, pressure and humidity. By "standard" temperature, pressure and humidity is meant, respectively, 3.0 to 30.0 degrees C., preferably less than 25 and most preferably about 4.0° C.; 1.0 to 3.0 atm., preferably about 1.0 atm. pressure; and 10.0 to 40.0%, preferably less than about 25%, relative humidity. In general, lower temperatures favor the entrapment of larger amounts of fluid additive, but the rate at which equilibrium is achieved is slower.

Another requirement is that the carbohydrate body used be substantially amorphous and undergo transformation from an amorphous to a more crystalline state at equilibrium conditions in the presence of the additive fluid. Also, the carbohydrate bodies must create internal space while undergoing the transformation from a less crystalline state to a more crystalline one.

While the initial carbohydrate bodies can be made in any way known to those skilled in the art, it is preferred that they be made by subjecting the carbohydrate, or a precursor thereof, to liquiflash or flash shear processing. In embodiments which include the shearlite particles described herein, the sugar particles become shearlite particles under liquiflash conditions.

In the flash shear process, a matrix product is formed by raising the temperature in the feedstock material which includes a non-solubilized carrier, such as a saccharide based material, until the carrier undergoes internal flow in the presence of a shear force. The feedstock is advanced and ejected while in internal flow condition, and subjected to disruptive shear force to form multiple masses. Exiting masses are cooled immediately after contact with the shear force and continue in a free-flow condition until solidified. The masses have a morphology different from that of the original feedstock. The final morphology is amorphous.

The flash shear process takes place in an apparatus which has features for heating a non-solubilized feedstock while simultaneously advancing it for ejection. First, a multiple heating zone twin screw extruder can be used for heating; a second feature is an ejector to put the feedstock in a condition for shearing. The ejector, preferably a nozzle, is in fluid communication with the heating means and is arranged to receive the feedstock while it has internal flow. See U.S. Pat. No. 5,380,473 to Bogue, et al., incorporated herein by reference, which shows such an apparatus.

Other liquiform techniques, such as flash flow and flash heat processing, can be used to make spherical bodies for use herein.

While the invention is not limited by the way the substantially amorphous carbohydrate bodies are made, the process used to make them must yield bodies that maintain an outer dimensional structural integrity during transformation. That is, the three dimensional silhouette of the carbohydrate body must remain intact during the transformation from a substantially amorphous to a crystalline state. Because of this maintenance of the dimensional framework, molecules undergoing transformation from their random amorphous arrangement to an organized crystalline arrangement will create additional internal spaces within the carbohydrate bodies, spaces in which additive molecules can be entrapped.

The most preferred embodiment uses substantially amorphous carbohydrate microspheres prepared by liquiflash processing described in commonly owned U.S. Pat. application Ser. No. 08/330,412 filed Oct. 28, 1994, which is incorporated herein by reference. Liquiflash processing subjects a feedstock to conditions of heat and pressure such that all resistance to liquid flow is eliminated. Once all resistance to liquid flow is gone, shear force is applied to the "liquiform" mass to separate discrete spheroidal particles therefrom. Such particles are called "shearlite particles". One process and apparatus for making useful microspheres is described in a U.S. patent application entitled "Apparatus for Melt Spinning Feedstock Materials having a Flow Restricting Ring" U.S. Ser. No. 08/854,344 filed May 12, 1997.

The carbohydrate bodies used herein are preferably pure untreated microspheres having diameters smaller than about 500 μm, generally smaller than about 400 μm, and preferably not greater than about 300 μm, with spheres of about 50 μm to about 250 μm diameter being very useful. Particles of about 50 μm to about 100 μm in diameter are operable.

Other methods for rendering carbohydrates or their precursors amorphous can be used and are contemplated.

Once one or more fluids or other additives have been entrapped in the bodies, they are useful in the delivery of bio-affecting agents to human consumers and other hosts. Conventional procedures for making comestible units, e.g., tableting, can be used to put the treated bodies in a form suitable for commercial purposes. Alternatively, they may be consumed "as is".

The preferred embodiments of the present invention have been described in yet further detail hereinbelow.

PREFERRED EMBODIMENTS

A particularly preferred embodiment uses shearlite particles which are prepared as described above.

Shearlite particles are ideally suited for contacting with an additive fluid, especially by immersion. They have a highly consistent spheroidal shape and a narrow range of size distribution, causing them to flow evenly and easily, and making them susceptible to smooth, uninterrupted handling in machines.

The carbohydrate bodies used are typically spheres having diameters between about 150 μm and about 250 μm.

The following examples illustrate the production of the amorphous carbohydrate bodies and their use in the present invention.

EXAMPLE I

Sucrose Microspheres

A liquiflash process was used to make sucrose microspheres. The apparatus used is described in U.S. Pat. No. 5,427,811, which is incorporated herein by reference. The opening between adjacent cable elements in the apparatus was 0.002 inches. The head, which was modified as disclosed in U.S. Ser. No. 08/854,344 discussed supra, was spun at 3600 rpm as it was heated to 180° C.

Figure 1B:
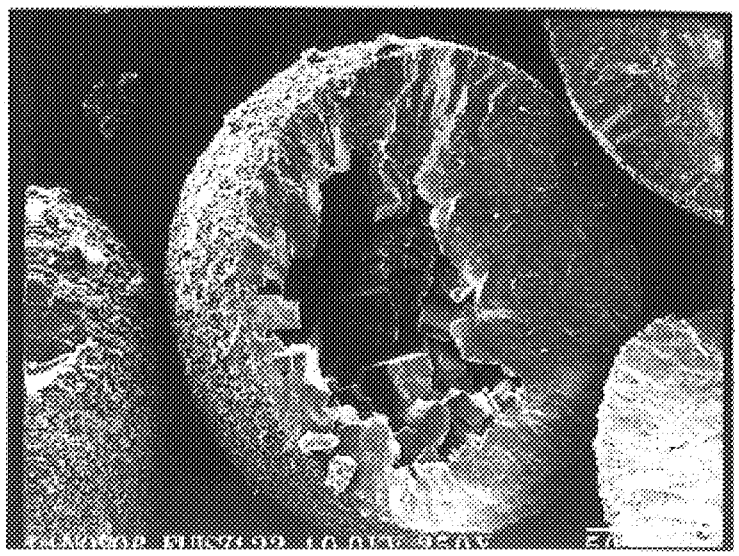
FIG. 1B is a 350× electron micrograph of a dissected crystalline sucrose microsphere showing one large void.

As the temperature peaked, the granulated sucrose was subjected to liquiflash conditions and exited the spinning head as physically solid amorphous microspheres, with no visible free volume space. The microspheres formed ranged in size from about 150 to about 250 μm in diameter. They recrystallized upon standing. One such microsphere is shown in FIG. 1A. Note the single large free volume space in FIG. 1B (the control). This is the representative crystal habit.

EXAMPLE II

Preparation of Loaded Carbohydrate Bodies

Amorphous sucrose microspheres produced using liquiflash conditions, as set forth in Example I, were then immersed in a pure peppermint oil (Rose Mitcham, #12223, provided by A. M. Todd Co.). The immersion took place at 20° C. for 3 days.

Figure 2A:
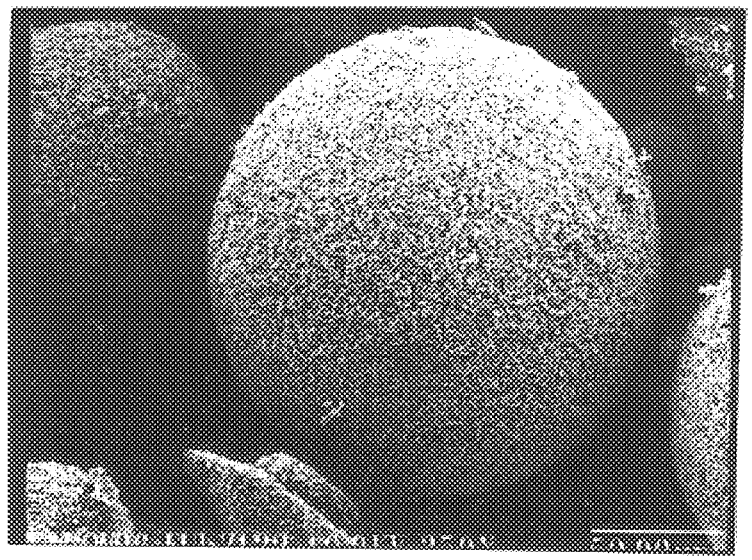
FIGS. 2A and 2B are electron micrographs at 350× magnification of, respectively, intact and dissected sucrose microspheres that are loaded with peppermint oil.

The microspheres were then vacuum filtrated to separate the loaded microspheres from the peppermint oil. The microspheres were then rinsed at least five (5) times with absolute (200%) ethanol to remove any residual flavor oil on the outer surface. As can be seen in FIG. 2A, which shows a loaded microsphere, the outer dimensional silhouette of the microsphere is maintained.

Figure 1C:
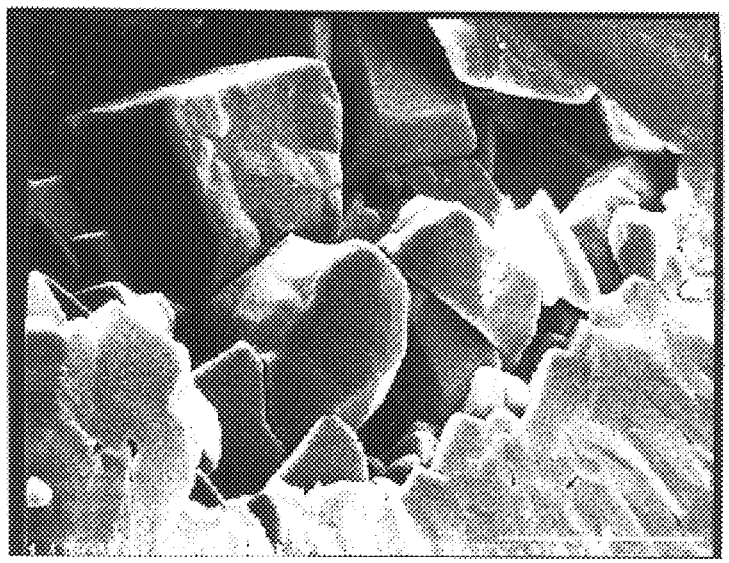
FIG. 1C shows a 1,400× electron micrograph of a dissected sucrose microsphere, showing free volume space therein.
Figure 2B:
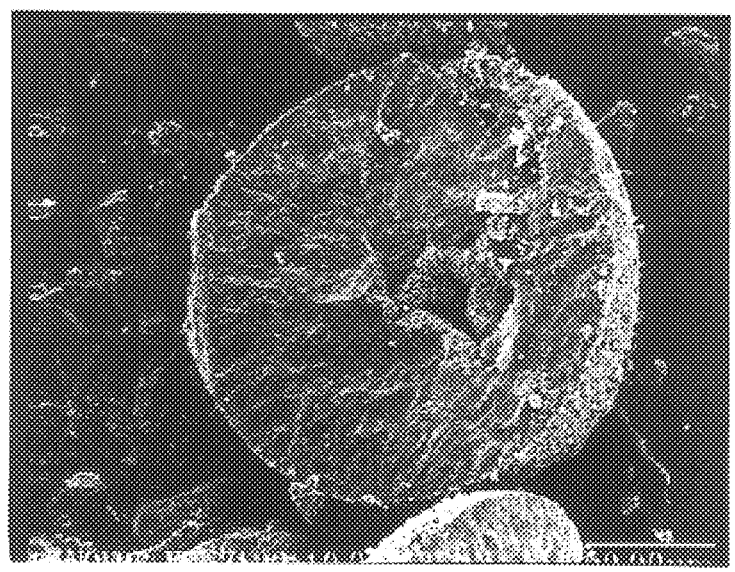
Figure 2C:
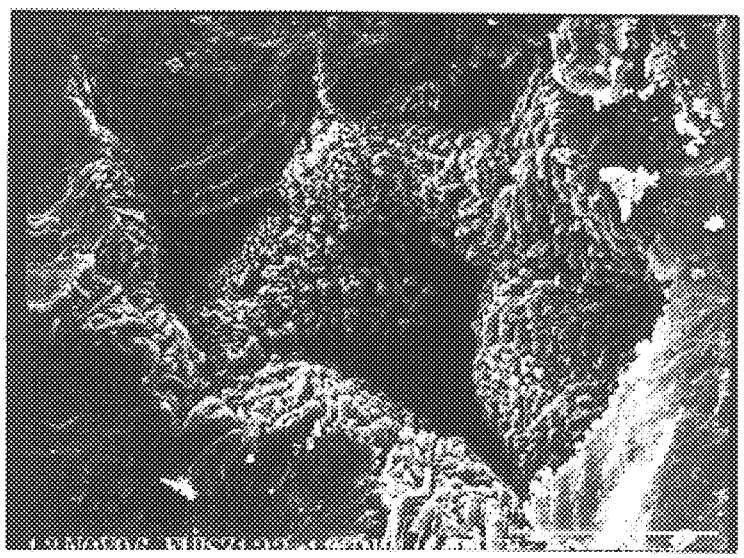
FIG. 2C is a 1,400× electron micrograph of a dissected sucrose microsphere which has been loaded with peppermint oil showing many small free volume spaces.

A sample of these loaded microspheres were dissected (i.e., crushed) to examine the internal structure of these loaded carbohydrate bodies. The dissected microspheres exhibited a structure that maintained the outer dimensional silhouette, as seen in FIGS. 2B and 2C. Also, the internal regions of the microspheres exhibited a crystalline structure that did not exist prior to contact. This new crystalline structure is evident in FIG. 2C, especially when compared to FIG. 1C.

A sample of the microspheres was then subjected to analytical assays to determine the amount of flavor oil entrapped in the spheres. The tests demonstrated that peppermint oil was loaded in the sphere in an amount of about 1.7% by weight. Furthermore, HPLC chromatograms indicated that even fine components of peppermint oil entrapped in the spheres displayed absolutely no distortion.

EXAMPLE III

Another experiment was performed using a procedure similar to that set forth in Example II. Sucrose spheres made using liquiflash conditions were immersed in a spearmint oil (#5 also provided by A. M. Todd Co.) at 4° C. for a period of 3 days.

The spheres were vacuum filtrated and washed with absolute ethanol.

EXAMPLE IV

A third experiment was undertaken in accordance with the protocol of Examples II and III. Sucrose spheres produced using liquiflash conditions set out in Example I were immersed in orange oil (# A-377, Givaudan-Roure) at 4° C. for a period of 3 days. The treated microspheres were vacuum filtrated and washed with absolute ethanol.

EXAMPLE V

Sucrose microspheres were made using the procedures and materials set out in Example I. However, the spheres were left standing for two months so they had substantially fully recrystallized.

The recrystallized microspheres were immersed at room temperature in anhydrous peppermint oil for three (3) days. The microspheres were then vacuum-filtered and rinsed with ethanol as set out in Example II.

A sample of the microspheres was assayed analytically to determine the amount of flavor oil therein. The tests showed that peppermint oil had been loaded in an amount of 0.043% by weight. Also, HPCC chromatograms showed that the components of the peppermint oil in the spheres displayed no distortion.

The recrystallized sucrose microspheres of this example imbibed much less peppermint oil (about 0.04%) when compared to the amount imbibed by the substantially amorphous spheres of Example II (which imbibed 1.7%).

Finally, organoleptic perception tests were conducted on samples of product taken from each of the examples. It was found that the organoleptic impact was of high quality and there was no perceived distortion of the flavor notes contained in the respective flavor oils.

The invention can be used in a variety of ways. Organoleptic tests performed on the comestible materials produced in the examples indicate that highly acceptable food and pharmaceutical products can be made using these bodies. Thus, delivery systems for bio-affecting agents and other materials to be ingested by consumers can be readily produced, stored and transported.

Also, the invention can be used for the storage and transportation of additives when their exposure to the environment is hazardous or destabilizing.

While there have been described what are presently believed to be the preferred embodiments of the invention, those skilled in the art will recognize that other and further modification may be made without departing from the true spirit of the invention, and it is intended to include all such further changes as fall within the scope of the invention as set forth in the appended claims.

We claim:

1. A method of entrapping an additive in carbohydrate bodies which comprises the steps of:

(1) contacting an anhydrous fluid comprising a non-solubilizing additive with pure untreated spherical carbohydrate bodies, wherein said carbohydrate bodies are substantially amorphous and are capable of forming at least a partially crystalline structure at equilibrium conditions, and (2) imbibing said fluid into crystallite spaces in said carbohydrate bodies, which spaces are formed as the bodies crystallize.

2. The method of claim 1 wherein said contacting comprises immersion of said carbohydrate bodies in said non-solubilizing additive fluid.

3. The method of claim 1 wherein said fluid is a liquid.

4. The method of claim 3 wherein said liquid is a flavor oil.

5. The method of claim 1 wherein said fluid further comprises at least one additional agent.

6. The method of claim 5 wherein said the additional agent is a bio-affecting ingredient.

7. The method of claim 1 wherein said carbohydrate body is formed from a carbohydrate precursor comprising a sugar.

8. The method of claim 7 wherein said sugar is sucrose.

9. The method of claim 1 which further comprises the step of subjecting a carbohydrate precursor to a process that forms microspherical carbohydrate bodies, prior to contacting said carbohydrate bodies with said non-solubilizing additive fluid.

10. The method of claim 9 wherein said process is liquiform processing.

11. The method of claim 9 wherein said process is flash flow processing.

12. The method of claim 11 wherein said flash flow processing is flash heat processing.

13. The method of claim 12 wherein said flash flow processing is flash shear processing.

14. The method of claim 1 wherein said bodies are kept at conditions of temperature, pressure and humidity that inhibit crystallization prior to step (1).

15. A delivery system comprising:

a carbohydrate body having a substantially solid external structure surrounding internal spaces created by at least partially crystallizing at equilibrium conditions; and an anhydrous fluid additive loaded and bound within said spaces.

16. The delivery system of claim 15 wherein said additive is a fluid.

17. The delivery system of claim 15 wherein said fluid is a liquid.

18. The delivery system of claim 17 wherein said liquid is a flavor oil.

19. The delivery system of claim 17 which comprises at least one additional agent.

20. The delivery system of claim 19 wherein said at least one additional agent is a bio-affecting ingredient.

21. The delivery system of claim 15 wherein said carbohydrate is a sugar.

22. The delivery system of claim 21 wherein said sugar is sucrose.

23. The delivery system of claim 15 wherein said carbohydrate body is a shearlite particle.

* * * * *